United States Patent [19]

Heinicke

[11] Patent Number: 4,666,606

[45] Date of Patent: May 19, 1987

[54] METHOD FOR ELIMINATING GREASE AND ODORS FROM SEWAGE SYSTEMS

[75] Inventor: Ralph Heinicke, Honolulu, Hi.

[73] Assignee: The Research Corporation of the University of Hawaii, Honolulu, Hi.

[21] Appl. No.: 688,961

[22] Filed: Jan. 4, 1985

Related U.S. Application Data

[60] Continuation-in-part of Ser. No. 530,689, Sep. 9, 1983, Pat. No. 4,543,212, which is a division of Ser. No. 329,953, Dec. 11, 1981, Pat. No. 4,409,144, which is a continuation-in-part of Ser. No. 870,919, Jan. 9, 1978, abandoned.

[51] Int. Cl.$^4$ .......................... C02F 1/68; C02F 3/00; C12N 1/00
[52] U.S. Cl. .................................. 210/632; 210/916; 210/610; 435/262
[58] Field of Search ............... 210/632, 606, 916, 610; 435/262

[56] References Cited

U.S. PATENT DOCUMENTS

| | | | |
|---|---|---|---|
| 3,506,582 | 4/1970 | Gertzman | 210/632 |
| 3,635,797 | 1/1972 | Battistoni et al. | 210/606 |
| 4,138,506 | 2/1979 | Eida et al. | 210/916 |
| 4,246,100 | 1/1981 | Starr | 210/916 |
| 4,541,986 | 9/1985 | Schwab et al. | 210/916 |

FOREIGN PATENT DOCUMENTS 2482130  11/1981  France ................................ 210/606

*Primary Examiner*—Benoit Castel
*Attorney, Agent, or Firm*—James C. Wray

[57] ABSTRACT

A method is disclosed for eliminating grease, sewage odor and hydrogen sulfide from restaurant grease traps and municipal sewage systems using xeronine. Xeronine works by stimulating the metabolism of the resident anaerobic and aerobic bacteria.

9 Claims, No Drawings

METHOD FOR ELIMINATING GREASE AND ODORS FROM SEWAGE SYSTEMS

This is a continuation-in-part of Ser. No. 530,689, filed Sept. 9, 1983, now U.S. Pat. No. 4,543,212 which is a division of Ser. No. 329,953, filed Dec. 11, 1981, now U.S. Pat. No. 4,409,144, which is a continuation-in-part of Ser. No. 870,919 filed Jan. 9, 1978, now abandoned.

BACKGROUND OF THE INVENTION

The invention relates to the chemistry of carbon compounds in the realm of molecular and microbiology. Furthermore, the invention relates to extracts or essences of undetermined constitution containing peptides of unknown chemical structure and enzyme or co-enzymes. The invention also relates to processes for preparing, activating, inhibiting, separating or purifying enzymes.

The invention relates to biochemical reactions leading to the production of a critical cell regulator which has great potential utility in pharmacology, microbiology, agriculture, and certain industrial operations such as fermentation, by-product recovery and sewage treatment. More in particular, the invention relates to a new alkaloid obtained by a complex series of enzymatic reactions from plant, animal and microbial extracts which contain specific proenzymes, specific enzymes, specific enzyme substrates and critical accessory factors. The invention also relates to processes for preparing, activating, inhibiting, separating or purifying the various enzymes involved in the formation of the alkaloid xeronine and for applying xeronine or a kit which will release xeronine in certain industrial, nutritional or pharmacological applications.

Parent U.S. Pat. No. 4,409,144, teaches that many commercial enzyme preparations which are used in pharmacology and industry and which are labeled and sold as proteases, peptidases, amylases or lysozymes actually owe their efficacy to chance contamination with the precursor system which produces xeronine. Since the amount of the xeronine precursor system varies between different batches of product made by the same manufacturer, the effectiveness of such products is unreliable. It is now proposed that either pure xeronine or a reliably standardized system or "kit" which releases xeronine be produced and used in place of these improperly described products.

The objectives of this continuation-in-part application are to amplify some additional methods of activating proxeroninase, to list some additional commercial sources of this enzyme, to give more specific details for processing several important commercial sources of xeronine, and to give further details about certain commercial applications of xeronine.

SUMMARY OF THE INVENTION

The invention proceeds upon the theory that the active ingredient xeronine is liberated from its precursor proxeronine by the action of a new type of enzyme termed proxeroninase. The invention is essentially a kit for producing xeronine in solution. The kit includes a source for proxeronine, a source for proxeroninase, means for mixing said source for proxeroninase with said source for proxeronine, and means for incubating a mixture of said source for proxeroninase and said source for proxeronine.

Certain plants contain commercial quantities of proxeronine and proxeroninogen in one tissue and active proxeroninase in another. For example the green fruit of *Morinda citrofolia* contains abundant proxeronine and proxeroninogen in the flesh whereas the mature but not senescent leaves contain proxeroninase. Similarly the gel of *Aloe vera* leaves is an excellent source of both proxeronine and proxeroninogen whereas the chlorophyllous surface layer of the leaf may be an excellent source of proxeroninase. (The amount of active enxyme in the green tissue varies with the weather.)

Proxeronine is a strange molecule which has been unrecognized in biochemistry notwithstanding the fact that it exists in relatively large amounts in plants, animals and microorganisms, and that it is relatively ubiquitous and very important in the metabolism of cells. The molecule has a molecular weight of about 4,000 and contains carbon, hydrogen, nitrogen, sulfur and oxygen. It contains neither sugars, amino acids nor nucleotides but does have a polyether chain. The only distinctive groups recognized so far are one or more carboxyl groups, a thioester group and a group which absorbs at 275 nm. When a pineapple plant becomes wet, this 275 nm group disappears suggesting that this part of the molecule has been converted into something else. The molecule is soluble in base to give a yellow brown solution; in acid it precipitates as a brown gum. it is very soluble in aqueous organic solvents such as methanol, ethanol, acetone, Cellusolve, etc. However, it is insoluble in pure alcohols or acetone. Thus, proxeronine may be extracted with 50% acetone or alcohol and then precipitated by adding additional solvent.

Proxeroninogens were among the first proteins to be crystalized. Abraham and Robinson crystallyzed lysozyme from egg white in 1937 and Emil Smith a plant lysozyme from papaya latex in 1954. Of course, at that time their correct functions were not known and they were called lysozymes. Proxeroninase was first isolated from milk in the forties as an alcohol soluble protein. The most feasible commercial source of this enzyme is whey even though the percentage of proxeroninase in the whey proteins is very low. The discovery that unboiled milk products, such as whey, spray dried whey powder, skim milk and whole milk are excellent sources of active proxeroninase has made a great difference in the practical application of xeronine. The nonsulfhydryl form of proxeronine, the form which occurs in extracts of natural products which have not been exposed to a pH above 6, is among the most stable of reactive biochemicals. Dilute solutions of proxeronine combined with a solubilizing agent, such as a wetting agent or 15 to 80% of an amphoteric solvent such as methanol, ethanol, or acetone but not restricted to these, can be kept at room temperature for years with no loss in activity.

The previous problem in using this excellent potential source of xeronine for industrial applications has been the difficulty in activating the proxeroninogen which frequently accompanies the proxeronine. Whereas, in the laboratory or in a well equipped food processing plant, the factors leading to the conversion of proxeroninogen to proxeroninase can be controlled, in most industrial environments such precise control is technically difficult. Discovering a dependable, environmentally acceptable and inexpensive source of active proxeroninase has opened up new and critical applications for xeronine.

A question might be raised concerning the possible role of active proxeroninase in milk. Apparently the developing young mammal requires an extra supply of xeronine. The natural substrate for mammal proxeroninase is proxeronine which occurs in the mucusal layer of the stomach.

Methods are described within whereby sources of proxeroninase are mixed with sources of proxeronine in order to arrive at liberated xeronine. This system may be utilized to liberate xeronine in beverages, to stimulate plants, and to control grease and hydrogen sulfide odors at waste water treatment systems.

DETAILED DESCRIPTION OF THE INVENTION

It can be said that many natural systems liberate xeronine. The limiting factor is frequently a supply of the enzyme proxeroninase. Although commercial bromelain contains proxeronine, it contains no active enzyme. Instead it contains an inactive form of the enzyme, proxeroninogen. This is a basic protein (isoelectric point of about 11) which is converted to an acidic protein, carboxyl-proxeroninogen, by an amidase. Two or three of the acidic monomers then aggregate in the presence of an appropriate level of calcium ions to form the active enzyme. The amidases which convert the inactive form into the acidic monomers are found in different tissues than those which store the proxeronine. Thus, grinding the entire leaves of aloes rather than following the usual custom of carefully scraping out the gel gave a juice which contained free xeronine. It could be that many of the successful herbal druggists unwittingly combined a good source of proxeronine with activated proxeroninase to provide a drug rich in xeronine.

The safest, the least expensive, and the most acceptable source of proxeroninase is whey. Whey could be used without additional purification for most applications, such as in packing houses, which process chicken, fish, starch or soy beans. It could also be used in the formulation of pills containing an acceptable source of proxeronine, whey and buffer salts. Another excellent source of potential proxeroninase is egg white. However, converting the proxeroninogen into proxeroninase is technically difficult.

One method of preparing crude proxeroninase from crude whey is to place 300 gallons of whey obtained from the tanks used to make cottage cheese or curd cheese in a 500 gallon tank with a cone bottom. 370 lbs of salt is then dissolved in the whey and the pH of the solution is raised to 6.5 with sodium hydroxide. The combination of 15% salt and higher pH precipitates most of the nucleic acids. The precipitates accumulate in the bottom of the cone leaving a clear supernatant solution. The salt retards the growth of bacteria so that the solution can be used for several weeks at room temperatures. Although the supernatant solution contains many ingredients other than proxeroninase, these are perfectly acceptable for almost all applications and need not be removed. For food and pharmaceutical applications properly processed spray dried whey powder could be used.

These sources of proxeroninase may be used to release xeronine from natural sources of proxeronine.

A test system was set up to test whether the enzyme proxeroninase in whey could release the xeronine from natural sources of proxeronine. The procedure involved using several plant extracts which were known from previous work to contain proxeronine. For an estimation of free xeronine, the ability of xeronine to increase the metabolism of microorganisms which had been partially inhibited with 0.5 g of urea/liter was used. Whey alone caused only negligible stimulation of carbon dioxide liberation from yeast. However, mixing whey with the substrates greatly increased the stimulation. (see Table 1)

TABLE 1

| Source of Proxeronine | Percent of Check Gas Production From A Yeast Suspension |
|---|---|
| Aloe Leaf Juice | 89 |
| Aloe Leaf Juice Plus Whey | 222 |
| (Whey Alone) | 110 |
| M. citrofolia Fruit Juice | 212 |
| M. citrofolia Fruit Juice Plus Whey | 575 |
| (Whey Alone) | 100 |
| Kelp Extract | 119 |
| Kelp Extract Plus Whey | 203 |
| (Whey Alone) | 109 |

Spray dried whey powder instead of fresh whey can also be used as a source of the enzyme. Since proxeroninase can tolerate temperatures up to 75 degrees Centigrade for five minutes, good processing techniques will not destroy too much of the enzyme. However, in evaluating different commercial batches of spray dried whey powder, it was found that about 15 to 30 percent of the batches had been overheated during processing. Not only was the activity low but the color was brown instead of the normal light yellow color. Setting color specifications on the whey powder would quickly eliminate this variation in quality.

Any unboiled milk product may be used as a source of proxeroninase, such as skim milk, or milk. However, whey is available commercially in large amounts at a low price. It contains more of the active enzyme and is accepted as a food additive by FDA.

In my previous patents concerning xeronine the isolation and purification of xeronine is discussed. However, the expensive and timely purification of xeronine is often unnecessary. Extracts of proxeronine and proxeroninase or proxeroninogen with accessory agents may be used to produce an extract of xeronine which in its crude form may be used in many ways.

The plant Noni, *Morinda citrofolia*, has been found to be very useful in the isolation of xeronine extracts. This plant is a member of the mulberry family which has been used by the Hawaiians as one of their principal herbal drugs. The fruit of Noni tastes bad and its pharmaceutical effects vary. That previous attempts to identify the pharmacological agent have been unsuccessful is understandable. Clinical data show that the active ingredient is produced by a series of enzymatic reactions which may occur if the juice passes rapidly through the stomach into the intestine. It may not occur if the juice remains in the stomach for one hour. Although Hawaiians use both the green and ripe fruit as well as extracts of leaves in the preparation of their herbal drugs, clinical data indicate that the green fruit has more desirable materials and fewer of the undesirable pigments and flavors. It has also been found that freezing the fruit before squeezing the juice improves juice recovery and decreases the viscosity of the juice. It is probable that more of the enzymes which are in the chlorophyll layer, such as depolymerases and some of the enzymes which produce active proxeroninase, are liberated during the freezing and pressing process. (See Table 2)

TABLE 2
Effect of Freezing on Juice Recovery from Noni Fruit

|  | Percent Crude Juice Recovery |
|---|---|
| Fresh, unfrozen fruit | 28.40 |
| Frozen, thawed fruits | 51.34 |

In the tests of Table 2 the fruits were pressed in a Carver press (static pressure) at 7.5 tons of pressure. The fresh fruit gave very little free juice. The recovered juice was mixed with plant tissue from the Carver press. A commercial screw press, operating at much lower pressures, and with greater rupture of cells would have pressed out more juice.

This freshly pressed juice contains either no active proxeroninase or only a small amount of active proxeroninase (see Table 1). The amount depends largely on how much of the chlorophyllous tissue in the peel of the fruit is ruptured during the freezing and pressing process.

Although green fruit juice contains less of the disagreeable flavors than ripe fruit (these are principally a mixture of short chain organic acids), it still is not suitable as a component of a health promoting beverage juice. In addition to small amounts of volatile acids, the juice contains several pigments. One is an intense blue-white fluorescent pigment, and another is a yellow-orange pigment in acidic solutions. However, this pigment turns black when the pH is raised in the presence of air. Even slightly acidic solutions which are kept for a long time turn black.

The Noni juice can be purified by passing an acidic juice over an acid washed nonionic polystyrene resin. The macroreticular form (XAD-2) is superior to the gel form. A column containing 625 ml of packed resin completely removed all of the odor and all of the fluorescent pigment from one liter of clear juice. When additional amounts of juice were passed over the column, some of the fluorescent pigment began to bleed through. This can be tolerated in a drink base.

Three distinct fractions can be recovered by XAD-2 fractionation of Noni juice, a percolate fraction, an acetone eluate fraction and a basic 50 percent acetone eluate fraction. If the original juice contains free xeronine, the free xeronine will appear in the percolate fraction. This fraction has a distinct but acceptable flavor. It blends well with any fruit juice without changing the flavor of the juice.

Special efforts can be made to increase the xeronine content of the percolate fraction by adding a source of proxeroninase. It has been found that Noni leaf extract or whey may be added to the juice. In addition, lowering the calcium level in the juice or increasing the activity of the small amounts of proxeroninase may also increase the xeronine content of the percolate fraction. Some FDA acceptable methods for lowering the concentration of calcium in the juice are to pass the juice over cation exchange resins or to add calcium sequestering agents, such as phosphate salts, uronic acids or citric acids. Some methods of increasing the activity of trace amounts of proxeroninase which might be present are to raise the temperature of the juice, adjust the pH of the juice to 4.5, or increase the length of time that the juice is held before it is processed.

After the XAD-2 column has been loaded, it is washed with water, and thoroughly drained. The column is then eluted with acetone. This operation removes the unwanted pigments and volatile organic acids.

The material remaining on the column after the acetone elution step consists primarily of a relatively pure mixture of proxeronine and proxeroninogen. These materials can be eluted from the column either with a 50 percent acetone solution, with a basic aqueous solution or with a basic 50 percent acetone solution. When the acetone is stripped from the solution at pH 4.5 or the basic solution is adjusted to pH 4.5, the proxeroninogen forms proxeroninase. At a pH near 4.5 this enzyme reacts with proxeronine to release xeronine.

Table 3 provides data which illustrate the fractionation of Noni juice on XAD-2. In this particular run some xeronine appeared in the acetone eluate fraction.

TABLE 3
Fractionation of Noni Juice on XAD-2 Macroreticular Resin

| Fraction | Total Xeronine Yeast Units | | |
|---|---|---|---|
|  | No Whey | Plus Whey | +W/−W |
| Original juice | 132,000 | 339,000 | 2.6 |
| Percolate solution | 81,000 | 78,000 | 1.0 |
| Acetone eluate | 16,800 | 31,500 | 1.9 |
| 50% Basic acetone eluate | 43,000 | 41,040 | 1.0 |

The recovery of xeronine in the three fractions was about 50 percent of the material applied to the column. A fourth fraction, which was eluted from the column with one percent sodium hydroxide, also contained xeronine. Due to the high concentration of sodium hydroxide this fraction was not purified in this experiment.

All of the recovered fractions in Table 3 would have been suitable sources of xeronine for blending with juice bases. The 50 percent basic acetone fraction had a bland flavor and a weak tea color. The original acetone eluate was both strongly colored and very odiferous. However, after the acetone had been removed, the pH of the solution adjusted to 4.0, and the solution rerun over a fresh XAD-2 column, all of the undesirable materials were removed.

The basic eluate is also suitable for reworking into material which would be suitable for pharmaceutical applications. To make a beverage base from *Morinda citrofolia* two liters of clarified juice made from pressed, frozen and then thawed green Noni fruits were passed over a 1,000 ml XAD-2 column which had been cleaned, rinsed with dilute acid and then water. The percolate solution from the XAD-2 column was initially clear and colorless. During the latter part of the run the solution had turned slightly turbid and had a trace oof fluorescent pigment. The flavor was bland. The yeast stimulating activity was high as was the physiological activity. Drinking about 50 ml of the undiluted juice caused noticeable contractions of the smooth muscles of the stomach. (This is one of the physiological actions of xeronine.)

When the percolate solution was mixed with pineapple juice at the rate of 90 parts of pineapple juice to ten parts of Noni percolate solution, taste testers were unable to tell which juice contained the Noni blend. None reported any noticeable stomach muscle contractions at this level of Noni.

Aloe has also been found to be useful in the isolation of xeronine extracts. The unique process described in this patent converts the thick viscous gel of aloe to a solution which has a viscosity similar to that of water. The process contributes a pleasant and distinctive acid flavor. This is pleasing by itself or it can be combined with fruit juices without masking the normal flavor of the fruit. Although the methods described can be used with any aloe leaf, they are especially valuable with aloes which can be machine harvested with a cutter bar and which will regenerate new plants from the roots of the cut plant.

*Aloe arborescens* has been found to be a suitable source. The plant is a vigorous grower giving yields per acre which are equal to or better than the more widely planted *Aloe vera*. The plant is well adapted to machine harvesting. By harvest time the first leaves are about six to eight inches above ground on a relatively narrow stem. Finally, the cut plant regenerates rapidly so that successive harvesting can be continued for many years before the field needs to be replanted.

Another species of aloe which may be adapted to machine harvesting is *Aloe saponaria*. In an experimental plot *Aloe saponaria* almost equalled the yield of *Aloe arborescens*. However, the plant growth was quite variable, some plants having all the leaves on stems which were upright whereas other plants had recumbent stems which would be impossible to harvest mechanically. Careful plant selection could probably give fields of uniformly upright plants. *Aloe saponaria* had more active hydrolases than *Aloe vera* and could be valuable to blend in with *Aloe vera* gel to lower the viscosity. However, *Aloe saponaria* did not have as much hydrolase as *Aloe arborescens*.

For all of the aloe experiments, the juice was prepared by grinding the aloe leaves or whole plants in a commercial Hobart meat grinder equipped with a medium plate. The puree was then pressed in a static pressure press or else frozen for later processing.

The crude aloe leaf juice contains a mixture of chlorophyll bodies, broken cell walls, fibers and debris. These can be removed by centrifuging. The supernatant solution is a low viscosity, yellow colored juice which has an intensely bitter flavor. The amount of soluble solids in the supernatant solution varies between 2 to 5 grams per 100 ml with an average value of 3. The pH range is between 3.4 to 4.5.

The pigments, primarily anthracene glycosides, cannot be tolerated in a beverage base. Not only are they intensely bitter, but they are potent purgatives. They can be removed completely by adsorption on XAD-2 or on carbon. With both adsorbents, the pH of adsorption should be between 3.5 to 4.5. At pH values near neutrality or higher, the pigments are not adsorbed. Also at pH values above 6.5, free xeronine will be adsorbed on the adsorbent together with the unwanted materials.

To determine whether pretreating the juice to lower the calcium level would increase the amount of proxeroninase formed, the juice was run over a specially prepared strong cation resin. All the resin was originally converted to the sodium form. Then before the column was used, the bottom one quarter of the column was treated with potassium hydroxide by upflow to replace the sodium ions. This type of column provides a juice high in potassium and low in sodium ions, an important nutritional consideration.

The juice feed to the strong cation column had a pH of 4.8; the collected percolate, a pH of 5.6. This was adjusted to pH 4.4 and run over an XAD-2 column. The percolate from this column was much less turbid than the juice treated only with XAD-2. However, the flavor was similar. (See Table 4)

TABLE 4

| Comparison of Different Resin Treatments of *Aloe arborescence* Juice | | |
|---|---|---|
| Treatment | Fraction | Biological Activity |
| None | Original Juice | 42,310 total units |
| Cation (C-20) Na K | Percolate | 400 total units |
| C-20 first; then XAD-2 | Percolate | 83,050 total units |
| XAD-2 only | Percolate | 60,000 total units |

This pretreatment with a K/Na cation exchange column definitely increased the amount of proxeroninase in the juice. No attempt was made to recover the free xeronine (42,310 units were adsorbed and removed on the cation column). Accordingly, the actual recovery of xeronine could have been even higher. In commercial operations, freshly pressed juice would have negligible free xeronine (See Table 1). For such juice this treatment would definitely be valuable.

In addition to XAD-2, several other classes of adsorbents at the ambient pH of the aloe juice were used. This data is given in Table 5.

TABLE 5

| Comparison of Different Types of Adsorbents for Removing Aloe Pigments When Used at the Rate of 20 g/100 ml (1) | | | |
|---|---|---|---|
| Adsorbent | pH of Supernatant | % Pigments Removed (2) | Color Supernatant |
| Carbon Beads (3) | 5.7 | 90.1 | Colorless |
| Darco G-60 | 5.3 | 97.3 | Colorless |
| Polyamide Powder | 4.3 | 63.3 | Pale Yellow |
| Silicic acid (200–400 mesh) | 4.1 | 20.8 | Yellow |
| Polystyrene gel sulfonic acid | 2.8 | 43.6 | Pale Yellow |

(1) The ambient pH of the aloe juice was 4.2.
(2) The changes in the absorbance at 295 nm, 269 nm, 253 nm, 226 nm and 210 nm between the original and the supernatant juice were averaged together to give a single value.
(3) The carbon beads (Ambersorb XE-348) were used at the rate of 40 g/100 ml of juice. These beads have been designed to be used in a column type operation and are regenerable.

Of these adsorbents carbon was the most efficient. In other tests, it was found that one percent concentration of carbon adsorbs 86 percent of the end UV absorbance and all of the yellow pigment. At 0.5 percent the color was still clear and the flavor was acceptable. However, at 0.25 percent carbon the aloe juice had color and had a distinctly bitter flavor, not too dissimilar from quinine water.

The pH is critical for effective use of carbon. Most commercial carbons have enough replaceable cations so that they raise the pH of the solution to which they are added. At pH six or higher, four percent carbon adsorbs 100 percent of the xeronine in the juice. Also, the effectiveness of the carbon in adsorbing the undesirable pigments decreases as the pH rises. Therefore, the pH of the carbon-aloe juice mixture should be checked and should be lowered to 3.8 to 4.5 with phosphoric acid to increase the adsorption of pigments and decrease the adsorption of xeronine.

An aloe beverage base may be made as follows: (1) the juice may be made by passing *Aloe arborescens* plants through a Hobart meat grinder with a medium size retainer plate; (2) the pulp is then frozen and then thawed; (3) the thawed pulp is then pressed in a Carver press and then clarified; and (4) two liters of juice at pH 4.1 is then passed over a 1,000 ml washed, slightly acidic XAD-2 column.

The percolate solution shows no trace of color throughout the run. However, the solution is slightly turbid. The juice has a pleasant acidic flavor with no aroma and no trace of bitterness. The yeast stimulation activity is high.

The aloe percolate solution is mixed with pineapple juice at the rate of 10-to-30 parts of percolate per 90-to-70 parts of pineapple juice. Taste testers were able to identify the fortified juice. However, all felt that the flavor was acceptable.

The utility of Noni juice or juice from aloe would be as a health food drink. This belief is based on the demonstration that samples of xeronine prepared by distillation, and which therefore could not possibly contain peptides, amino acids or steroids, acted as excellent anti-inflammatory agents when injected into mice. In addition, xeronine inhibited the in vitro aggregation of blood platelets by adenosine diphosphate, caused the debridement of burn eschars on mice, stimulated the partial breakdown of wheat grits, and caused the aggregation of casein. All of these are reactions formerly imputed to such proteases as "bromelain" pancreatin, and *Serratia marcescens* protein. Therefore, standardized preparations of xeronine or blends containing xeronine should be more effective for all of the present medical, nutritional, and industrial applications of bromelain and the other enzymes. This is especially true since these are improperly standardized, and therefore, unreliable in performance.

There are now several new and important applications for xeronine. My demonstration that the active ingredient in many of the pharmacologically active enzymes and in many of the effective folklore drugs is an alkaloid deemed xeronine, and that this alkaloid can be recovered from animal and bacterial sources, indicates that this alkaloid is a critical normal metabolic coregulator. Therefore, one could theorize that xeronine would be an effective antidote against alkaloid poisoning and addiction. In support of this it was found that a relatively pure sample of xeronine was an almost perfect antidote for tetrodotoxin, the most toxic alkaloid known. This confirmation of the theory led to the prediction that xeronine should be a specific cure for nicotine and hard drug addiction. Crude preparations of xeronine were tested on confirmed smokers with a 90% cure rate and no consequential tension involved during the withdrawal period. With hard core drug addicts, xeronine should provide a true cure with no withdrawal symptoms. Preliminary tests with crude preparations of xeronine have shown complete cures of hard core drug addicts with no withdrawal symptoms and with no dependency on a substitute alkaloid.

Another critical potential application for xeronine is for the alleviation of the symptoms of one type of senility. This observation was originally made by Gus Martin with a sample of enzyme which was prepared in the early phases of the xeronine research. This particular sample was made into pills and given to a woman who had been senile, uncomprehending, immobile, and incontinent for three months. Two hours after taking the pill she sat up in bed, asked why she was there and began asking for her family. As long as she was taking the pills, she was a normal, functioning person and took a very active part in the hospital program. When the supply of this batch of pills ran out, an "improved" batch of bromelain pills was substituted. Three days later she lapsed into her former senile state. Until the recent work on xeronine, repetition and explanation as to why this one batch of bromelain behaved so spectacularly was elusive.

Another important new application for xeronine will be as a general stimulant or tonic. In the tetrodotoxin experiment mentioned above, the control mice which had been injected with only xeronine became very alert and explored their cage for about a half an hour before they also burrowed into the shavings as the saline injected mice had done immediately after being injected. Based on this behavior in mice, I drank a solution of xeronine containing about 50 times as much xeronine as the mice had received. The pleasant, stimulating, alert feeling lasted until about three o'clock in the morning. This is a response which is similar to that reported by Russian scientists for extracts of high quality ginseng or Eleuthrococcus.

In summary, as far as the medical applications of xeronine are concerned, the discovery that xeronine can counteract the effects of foreign alkaloids will suggest many new and important applications in medicine. Also, another discovery which will have important medical applications is the finding that xeropine acts as a coregulator for many hormone actions. This suggests that the body has a two component system for regulating and integrating the metabolism of different tissues: (1) hormones, which are secreted into the blood stream and contact all tissues; and (2) xeronine, which is produced locally by the tissue and determines whether or not that tissue will respond to the presence of the hormone in the blood. Both factors must be present for a response to occur. This theory suggests that many problems, such as diabetes, may be caused either by a lack of the hormone, insulin, or by the lack of xeronine in the cell membrane at the local level. Both must be present for the cell to properly absorb and metabolize glucose.

Combining sources of xeronine or proxeronine and proxeroninase with a palatable juice provides people who wish to take xeronine for therapeutic purposes with a pleasant, effective and safe drink. This drink would be similar in form to some of the old folklore remedies but without any of the highly variable results. A health food beverage containing xeronine and proxeronine would be both reliable and highly palatable. Effective health drinks based on xeronine must either have free xeronine in the drink or have proxeronine and potential proxeroninase and be taken on a empty stomach. Of these two options, only the first can be relied on. The second option is unmanageable. Any juice may be combined with the xeronine-rich blending base. Pineapple juice, being especially rich in other health promoting materials, is especially useful. Other possibilities are guava, orange, apple, cider, lemon, grape, vegetable, and others. Still other possibilities are beer and wines.

The possible benefits from drinking such fortified juices are many and cover all the reported benefits from taking pills such as bromelain or extracts of Eleuthrococcus. The Russians have made extensive physiological studies on the effect of extracts of Eleuthrococcus on physical vigor, the ability to do without sleep, mental alertness, and the ability of the body to withstand stresses from heat and cold. Since xeronine has been isolated from ginseng, a plant related to Eluethrococcus, it is probable that when Eleuthrococcus extracts are effective, they are so because they are a potential source of xeronine.

Xeronine and proxeronine have other applications other than being used as components of health-promoting drinks. For instance, it has been found that concentrated solutions of proxeronine, such as 20-30 ppm w/w, if sprayed onto the leaves of certain plants can have strange effects on blossoming and setting of seeds and fruit. For example, on a mature, fruit bearing papaya tree, one application of this concentration of proxeronine inhibited fruit set for three months. During this time the tree blossomed profusely over a two to three foot span of the trunk, a most unusual blooming habit. Then, at the end of three months all the blossoms set fruit. This fruiting over such a distance of trunk is also unusual.

This fruit inhibiting action can be prevented, or if it has already occurred, can be reversed by applying the same concentration of proxeronine mixed with several percent of whey and enough ammonium hydroxide to raise the pH to about 7. This combination, which liberates free xeronine, causes plants to both blossom and to set fruit. This occurs on both young plants which have not yet begun to set fruit and also on old plants which have previously been sprayed with proxeronine and which have blossoms but no fruit.

The fruit set stimulating action is limited to those blossoms which are open when the plants are sprayed. Thus, by alternating the spraying of peroxeronine to inhibit with the spraying of the combination of proxeronine and whey to encourage fruit set, one can produce bands of fruit along the stem. Being able to control fruit development can enable a farmer to avoid dumping fruit on an oversupplied market, as well as, to stimulate fruit set when prices are high.

Using proxeronine to inhibit seed and fruit development also has certain important commercial applications. For example, many ornamental trees are grown for their attractive flowers. The Royal Poinciana, shower trees, and oliver trees come readily to mind. Unfortunately, these trees also have unwanted seed pods or unwanted fruit which are unsightly. However, if the trees are sprayed once a week during the blossoming period, the blossoming period is lengthened and seed development is completely inhibited. This spray does not harm the honey bees which are attracted to the blossoms and has only positive environmental effects.

It is felt that xeronine acts as a possible coregulator with secreted hormones in plants. For example, in the pineapple plant xeronine converts certain precursors of hydrolytic enzymes into the active form. Thus, xeronine, through its action in forming active hydrolases, converts stored food material, such as starch, proteins, and organic phosphorous compounds in the leaves or stems into soluble sugars, amino acids and phosphorus. These can be used either to produce new growth or to mobilize food for storage in seeds or tubers.

This action has great utility. If applied to the plant it increases the amount of food stored in such vegetables as peas, corn, lima beans, beans, wheat, rice, etc. If applied to the harvested seeds before they are processed, it activates the amylases and partially converts the starch into sugar, thus producing a sweeter and more tender product. Such an action also has great value in hastening the germination of seeds by stimulating the conversion of the stored food products into simple useable molecules.

Xeronine is also useful in eliminating grease, sewage odor and hydrogen sulfide from restaurant grease traps and municipal sewage systems. Xeronine works by stimulating the metabolism of the resident anaerobic and aerobic bacteria. Unfortunately, xeronine has a relatively short shelf life under commercial conditions; by contrast, proxeronine is stable for many years even if it is kept in solution at room temperatures. Thus, mixing proxeronine and proxeroninase at the site of use is commercially more satisfactory than attempting to use the more labile xeronine.

In certain applications, such as eliminating the build up of grease in restaurant grease traps, the system normally contains sufficient proxeroninase so that only proxeronine need be added. Most restaurants dump enough milk into the sink when they clean their customers' trays to supply an adequate amount of proxeroninase. However, some grease traps, for example those serving a meat cutting room, can have the same amount of proxeronine added to a similar sized grease trap, but to no avail. A source of proxeroninase is needed.

The amount of proxeronine and proxeroninase required to prevent the build up of grease in an average grease trap is truly miniscule. The 5% kelp extract used as a source of proxeronine in the experiments reported in this section contained 125 ppm (w/w) proxeronine. A small sized grease trap with a daily throughput of 500 gallons of sink waste requires approximately one pint of kelp extract per day. This amounts to about 50 mg of proxeronine per day or about 1.4 micrograms per gallon of kitchen waste.

The device which was used to combine proxeroninase and proxeronine at the site of use was simple, effective and reliable. Both the whey-salt solution and the 5% kelp extract were metered into a one gallon jug for small systems and into a 5 gallon jug for larger systems. Since the whey-salt solution was denser than the 5% kelp extract, whey was added at the top of the jug and the kelp at the bottom. To increase the counterflow time, a metal spiral band was placed around the metal tube leading to the bottom of the jug. For grease traps the jug was suspended over the inlet T; for municipal sewage plants the jug was suspended in the stream leading to the odor producing tank or trickling filter. Depending upon the flow rates chosen, the holding time in the jug varied between 1 to 4 hours. This was an adequate time for proxeroninase to release xeronine.

If all the grease traps of the restaurants in an area are treated with proxeronine, the stimulating action of xeronine would extend throughout the collecting system and into the sewage treatment plant. The effect at the plant shows: (1) increased throughput of sewage as the formerly grease clogged pumps begin to operate more efficiently; (2) a sewage plant effluent which has a lower solid content and a lower bacterial count; and (3) fewer odors. However, if the proxeronine is added only at the sewage plant, then absolutely no beneficial results occur. By the time the sewage reaches the treatment plant, no proxeroninase remains to release xeronine from the added proxeronine.

In a large scale experiment at a 5.5 million gallon a day sewage treatment plant, three futile months were spent attempting to control the liberation of hydrogen sulfide gas from the trickling filter by varying the amount and the place of application of proxeronine. What had worked so dramatically in restaurant grease traps in eliminating odors and grease was a complete failure at the sewage treatment plant. However, after the 5% kelp extract and whey were combined and incubated, this mixture was then added to the stream going to the trickling filter. The level of hydrogen sulfide gas liberated from the filter dropped sharply. (See Table 6). This treatment gave an odor control which was far superior to the conventional hydrogen peroxide treatment. Also, in contrast to the hydrogen peroxide treatment, all of the materials used in the treatment were safe with no special safety precautions needed. A critical factor to be considered by municipalities and their surrounding communities is the projected cost of this type of odor control which should be considerably less than that of any of the conventional chemical treatments.

TABLE 6

Comparison of the Air Hydrogen Sulfide Level at the Standpipe of a Trickling Filter of a Municipal Sewage Treatment Plant After Different Treatments

| Treatment | Day | ppb Hydrogen Sulfide |
| --- | --- | --- |
| None | 00 | 25 Average |
| 5% kelp extract | 0 | 22 Average |
| 5% kelp extract + whey | 1 | 8 |
| " | 2 | 3 |
| " | 3 | 2 |
| None | 4 | 8 |
| None | 5 | 17 |

Having described my invention with particularity and having described the utility thereof, I now set out the scope and spirit of my invention as embodied in the following claims.

What I claim is:

1. The method for treating sewage treatment systems for elimination of grease, hydrogen sulfide, and sewage odors where said systems contain an adequate source of proxeroninase, comprising the step of:
   (a) adding a commercial source of proxeronine into various grease traps located along the sewage treatment system, the addition of proxeronine to proxeroninase being in a sufficient quantity to yield xeronine which stimulates metabolic function of aerobic and anaerobic bacteria which breaks down grease.

2. The method of claim 1 where said adding is performed by means of an automatic dispenser.

3. The method of claim 1 where said commercial source of proxeronine further comprises 5% w/w kelp extract, *Morinda citrofolia* fruit juice, the juice pressed from pineapple stems, pineapple cannery.

4. The method of claim 1 wherein the proxeronine is added in quantities of approximately 1.4 micrograms per gallon of waste running through the sewage treatment systems.

5. A method for eliminating grease, hydrogen sulfide, and sewage odors from sewage treatment systems containing no adequate source of proxeroninase, comprising the steps of:
   (a) mixing a source of proxeroninase with a source of peroxeronine; and
   (b) adding said mixture to a sewage treatment system, the proxeroninase and the proxeronine being in a sufficient quantity to yield a sufficient quantity of xeronine to stimulate the metabolism of anaerobic and aerobic bacteria which breaks down grease.

6. The method of claim 5 where said source for proxeroninase further comprises whey.

7. The method of claim 6 where said source for proxeronine further comprises kelp extract.

8. The method of claim 6 where said adding is performed by means of an automatic dispenser.

9. The method of claim 5 wherein the proxeronine is added in quantities of approximately 1.4 micrograms per gallon of waste running through the sewage treatment systems.

* * * * *